United States Patent
Dooney, Jr. et al.

(10) Patent No.: US 8,444,680 B2
(45) Date of Patent: May 21, 2013

(54) POLYAXIAL BUSHING FOR LOCKING PLATE

(75) Inventors: Thomas Dooney, Jr., Naples, FL (US); John A. Sodeika, Naples, FL (US)

(73) Assignee: Arthrex, Inc., Naples, FL (US)

( * ) Notice: Subject to any disclaimer, the term of this patent is extended or adjusted under 35 U.S.C. 154(b) by 233 days.

(21) Appl. No.: 12/941,516

(22) Filed: Nov. 8, 2010

(65) Prior Publication Data

US 2011/0112536 A1    May 12, 2011

Related U.S. Application Data

(60) Provisional application No. 61/259,500, filed on Nov. 9, 2009.

(51) Int. Cl.
*A61B 17/80* (2006.01)

(52) U.S. Cl.
USPC ............................. 606/290; 606/289; 606/70

(58) Field of Classification Search
USPC .......................................... 606/289, 290, 288
See application file for complete search history.

(56) References Cited

U.S. PATENT DOCUMENTS

| | | | |
|---|---|---|---|
| 5,151,103 A | 9/1992 | Tepic et al. | |
| 5,735,853 A | 4/1998 | Olerud | |
| 5,954,722 A | 9/1999 | Bono | |
| 6,017,345 A | 1/2000 | Richelsoph | |
| 6,890,335 B2 | 5/2005 | Grabowski et al. | |
| 7,179,260 B2 | 2/2007 | Gerlach et al. | |
| 7,195,633 B2 | 3/2007 | Medoff et al. | |
| 7,229,443 B2 | 6/2007 | Eberlein et al. | |
| 7,604,657 B2 | 10/2009 | Orbay et al. | |
| 7,682,379 B2 | 3/2010 | Mathieu et al. | |
| 8,172,885 B2 * | 5/2012 | Songer et al. | 606/290 |
| 2004/0167522 A1 | 8/2004 | Niederberger et al. | |
| 2004/0225291 A1 | 11/2004 | Schwammberger et al. | |
| 2005/0043736 A1 | 2/2005 | Mathieu et al. | |
| 2005/0143742 A1 | 6/2005 | Porcher | |
| 2006/0235399 A1 * | 10/2006 | Carls et al. | 606/69 |
| 2007/0010817 A1 | 1/2007 | de Coninck | |

(Continued)

FOREIGN PATENT DOCUMENTS

| | | |
|---|---|---|
| WO | WO 03/055401 A1 | 7/2003 |
| WO | WO 2007/050796 A2 | 5/2007 |

*Primary Examiner* — Andrew Yang
(74) *Attorney, Agent, or Firm* — Dickstein Shapiro LLP

(57) ABSTRACT

A bone plate with a new design that prevents the bushing from rotating and/or dislodging from the screw hole during screw insertion. The plate is provided with through-holes having internal walls with at least one flat that is configured to align with a corresponding flat provided on the outer wall of the bushing. The bushing is inserted by orienting the bushing in a direction perpendicular to the through-hole of the plate so that the center of the bushing is aligned with the center of the through-hole and the flat on the bushing is aligned with the flat on the through-hole of the bone plate. The bushing is introduced into the through hole until the centers are aligned, and then the bushing is rotated about 90 degrees so that the bushing is captured within the through-hole of the plate. Once captured, the bushing cannot rotate, dislodge from, or come out of the plate unless the bushing is turned 90 degrees. The flat on the bushing mates with the flat on the internal wall of the hole (screw hole) to prevent it from rotating within the screw hole, and avoiding the need for a bushing guide during screw insertion.

19 Claims, 4 Drawing Sheets

U.S. PATENT DOCUMENTS

| | | |
|---|---|---|
| 2007/0118126 A1 | 5/2007 | Medoff et al. |
| 2007/0162020 A1 | 7/2007 | Gerlach et al. |
| 2007/0276386 A1 | 11/2007 | Gerlach et al. |
| 2008/0114359 A1 | 5/2008 | Murner et al. |
| 2008/0119895 A1 | 5/2008 | Manceau |
| 2008/0172094 A1 | 7/2008 | Mathieu et al. |
| 2009/0088807 A1 | 4/2009 | Castaneda et al. |
| 2009/0192549 A1* | 7/2009 | Sanders et al. ............... 606/280 |

* cited by examiner

SECTION A-A

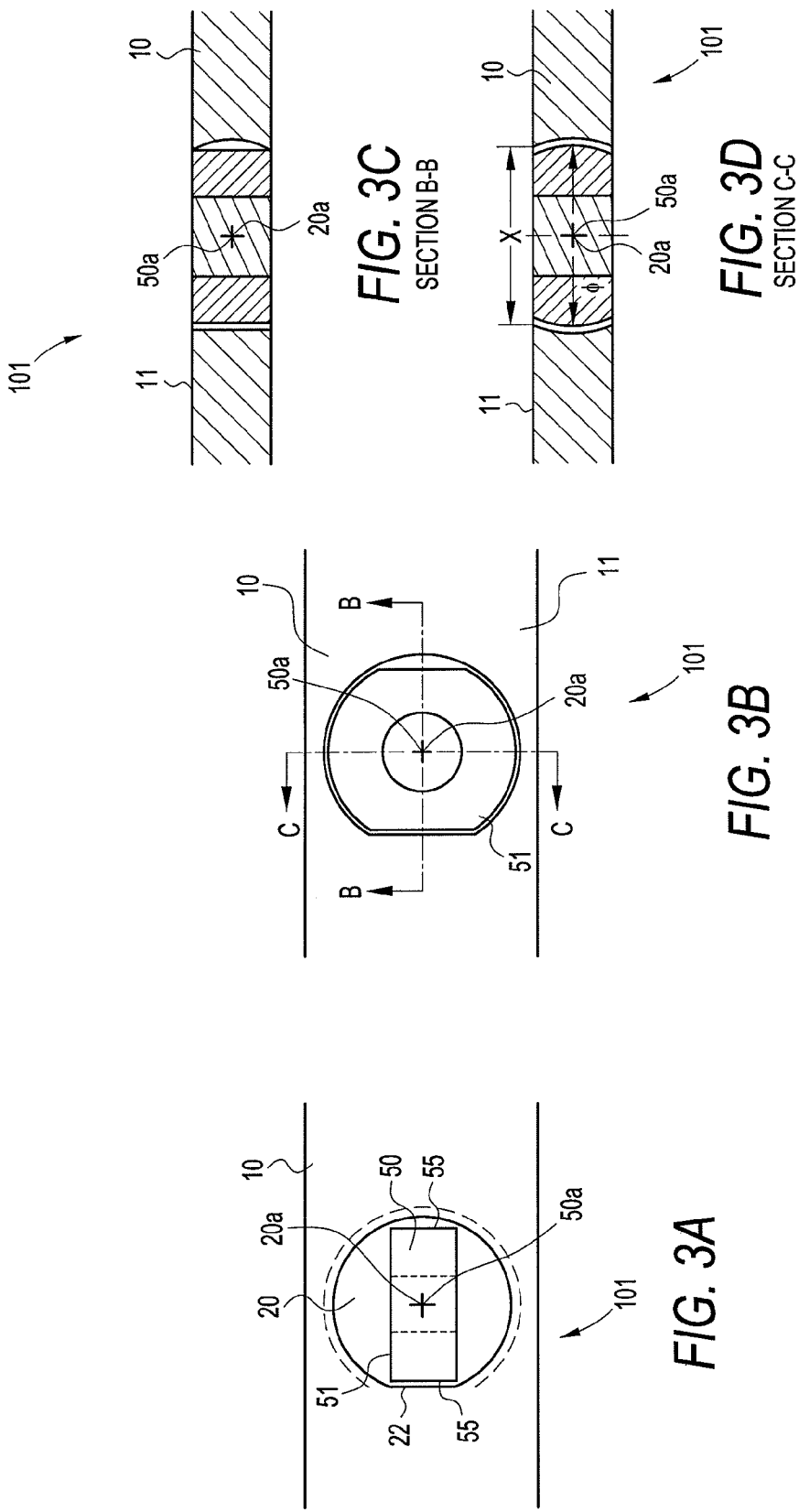

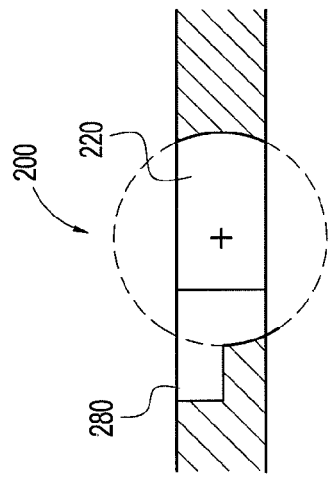
FIG. 4A
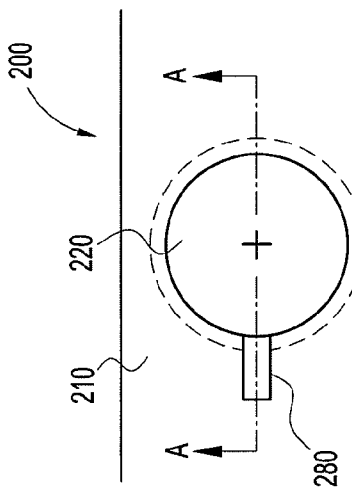
FIG. 4B
SECTION A-A
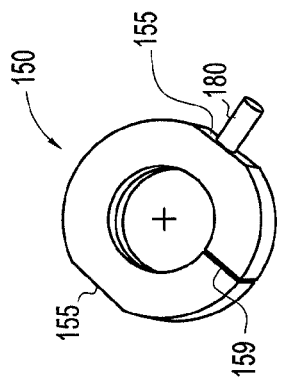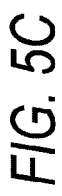
FIG. 5C
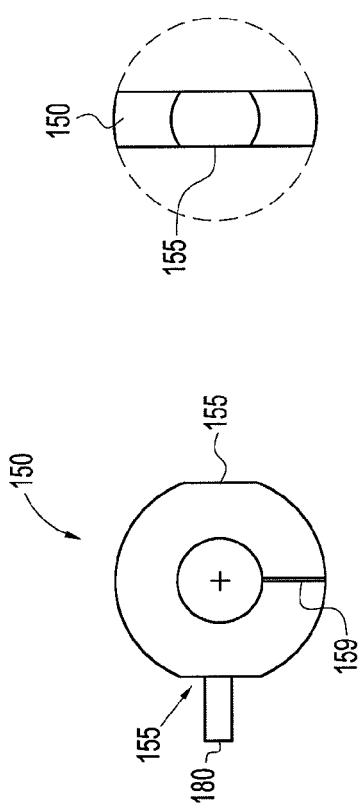
FIG. 5B
FIG. 5A

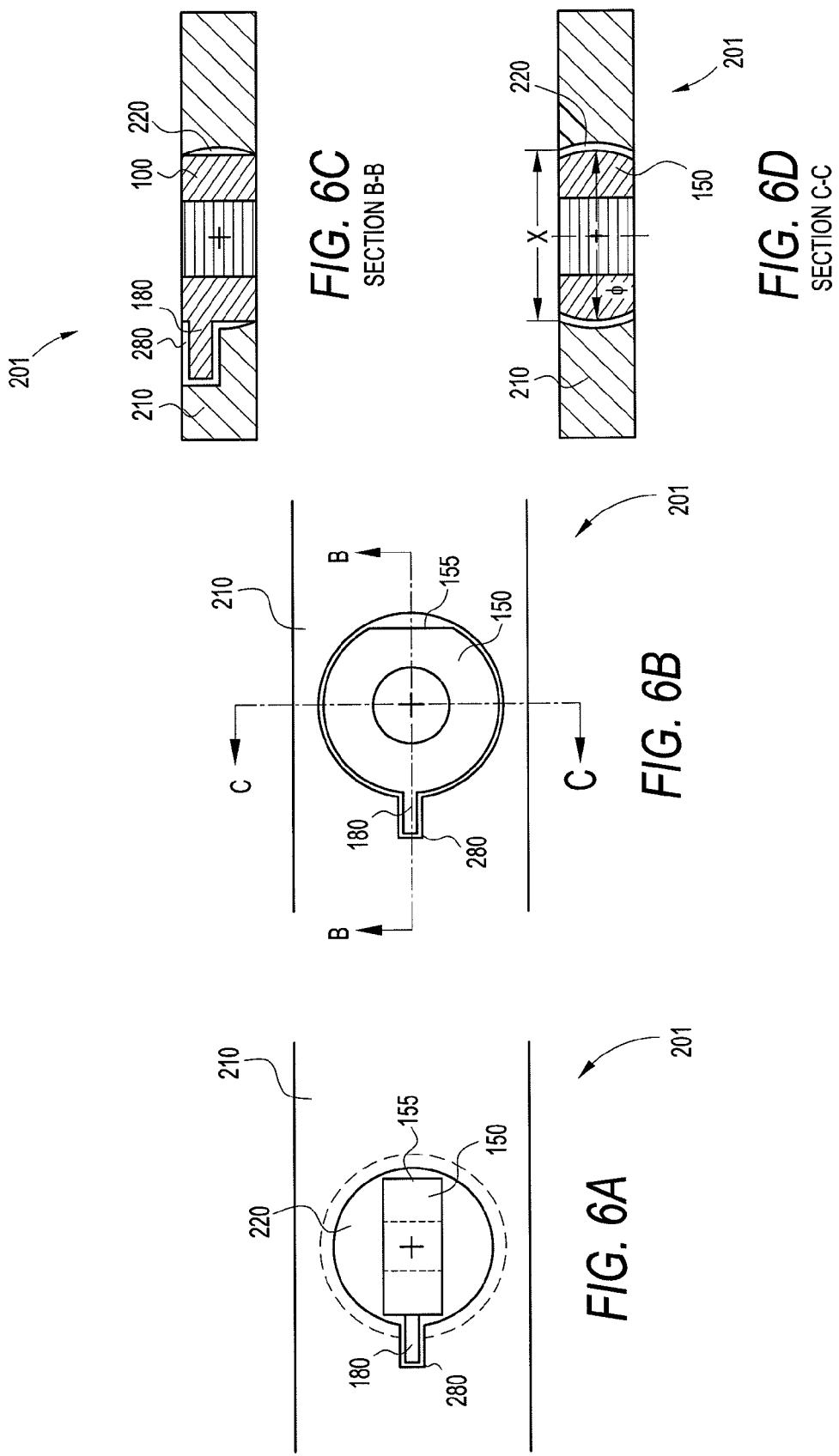

POLYAXIAL BUSHING FOR LOCKING PLATE

CROSS-REFERENCE TO RELATED APPLICATIONS

This application claims the benefit of U.S. Provisional Application No. 61/259,500, filed Nov. 9, 2009, the entire disclosure of which is incorporated by reference herein.

FIELD OF THE INVENTION

The present invention relates to bone plates having locking bushings.

BACKGROUND OF THE INVENTION

Bone plates known in the art are typically provided with self-tapping bone plate screws that allow the bone plate to be secured to a surface of the bone. The screws are inserted through holes, which are formed into the bone plate and which contain washers or bushings that are rotatable in the holes. When the screw is inserted, the head of the screw typically spreads the bushing (for example, a split-sleeve bushing) as the screw advances and ultimately locks the bushing to the bone plate. The bushings may provide for variable angles of insertion for the screws. During insertion of the screws into the bone plate, the bushings may inadvertently rotate within the screw hole or even dislodge from the through-hole of the bone plate, causing a delay in the surgical procedure.

Accordingly, there is a need for a bone plate provided with a new design that prevents the bushing from rotating and/or dislodging from the screw hole during screw insertion. Also needed is a bushing design that allows the screw to be locked at variable angles.

BRIEF SUMMARY OF THE INVENTION

The present invention provides a bone plate, preferably a humeral plate, with a new design that prevents the bushing from rotating and/or dislodging from the screw hole during screw insertion. The bushing design of the present invention also allows the screw to be locked at variable angles.

The plate of the present invention is provided with through-holes having internal walls with at least one flat that is configured to align with a corresponding flat provided on the outer wall of the bushing. The bushing is inserted by orienting the bushing in a direction perpendicular to the through-hole of the plate (screw hole) so that the center of the bushing is aligned with the center of the through-hole and the flat on the bushing is aligned with the flat on the through-hole of the bone plate. The bushing is introduced into the through-hole until the centers are aligned, and then the bushing is rotated about 90 degrees so that the bushing is captured within the through-hole of the plate. Once captured, the bushing cannot rotate, dislodge from, or come out of the plate unless the bushing is turned 90 degrees. The flat on the bushing mates with the flat on the internal wall of the hole (screw hole) to prevent it from rotating within the screw hole. This important aspect avoids the need for a bushing guide during screw insertion.

In an alternate embodiment, the bushing may be provided with an optional post in addition to the flat to prevent the bushing from rotating.

These and other features and advantages of the invention will be more apparent from the following detailed description that is provided in connection with the accompanying drawings and illustrated exemplary embodiments of the invention.

BRIEF DESCRIPTION OF THE DRAWINGS

FIG. 3A illustrate the step of inserting the bushing of FIGS. 2A-2C within the through-hole (screw hole) of the plate of FIGS. 1A-2B, and according to an exemplary method of the present invention of assembling the bushing with the plate to form a plate/bushing assembly (illustrating the bushing oriented about 90 degrees relative to the plate, with the flat of the bushing aligned with the flat of the plate, and with the center of the bushing coinciding with the center of the plate).

FIG. 3B illustrate a step of assembling the bushing to the plate subsequent to that shown in FIG. 3A (illustrating the rotation of the bushing within the through-hole (screw hole) of the plate, for about 90 degrees, to constrain and lock the bushing within the through-hole of the plate).

FIG. 3C illustrate a cross-sectional view of the plate/bushing assembly of FIG. 3B, taken along line B-B.

FIG. 3D illustrate a cross-sectional view of the plate/bushing assembly of FIG. 3B, taken along line C-C.

FIG. 4A illustrates a partial top view of a bone plate of the present invention with a through-hole (screw hole) and a pin slot, according to a second embodiment of the present invention;

FIG. 4B illustrates a cross-sectional view of bone plate of FIG. 1A taken along line A-A;

FIG. 5A illustrates a top view of a bushing of the present invention provided with a pin and for use with the bone plate of FIG. 1A, and according to a second embodiment.

FIG. 5B illustrates a left-side lateral view of the bushing of FIG. 5A.

FIG. 5C illustrates a perspective view of the bushing of FIG. 5A.

FIG. 6A illustrate the step of inserting the bushing of FIGS. 5A-2C within the through-hole (screw hole) of the plate of FIGS. 4A-2B, and according to an exemplary method of the present invention of assembling the bushing with the plate to form a plate/bushing/pin assembly (illustrating the bushing oriented about 90 degrees relative to the plate, with the pin of the bushing aligned with and positioned within the pin slot of the plate, and with the center of the bushing coinciding with the center of the plate).

FIG. 6B illustrate a step of assembling the bushing to the plate subsequent to that shown in FIG. 6A (illustrating the rotation of the bushing within the through-hole (screw hole) of the plate, for about 90 degrees, to constrain and lock the bushing within the through-hole of the plate).

FIG. 6C illustrate a cross-sectional view of the plate/bushing assembly of FIG. 6B, taken along line B-B.

FIG. 6D illustrate a cross-sectional view of the plate/bushing assembly of FIG. 6B, taken along line C-C.

DETAILED DESCRIPTION OF THE INVENTION

Figure 1A:
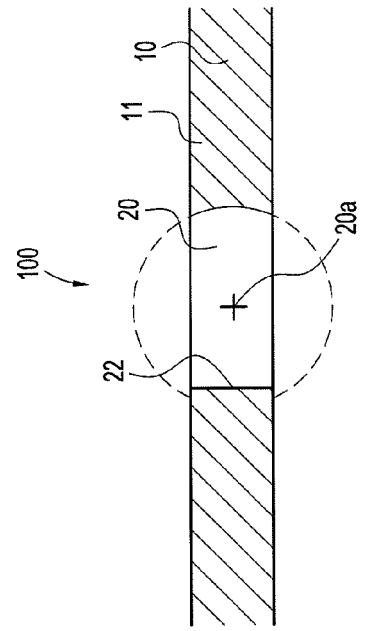
FIG. 1A illustrates a partial top view of a bone plate of the present invention with a through-hole (screw hole) according to a first embodiment of the present invention.

The present invention provides a bone plate with a locking design that prevents the bushing from rotating and/or dislodging from the screw hole during screw insertion. The design of the plate and bushing of the present invention also allows the screw to lock at variable angles.

Referring now to the drawings, where like elements are designated by like reference numerals, FIGS. 1-6 illustrate a bone plate 100, 200 of the present invention provided with bushings 50, 150 that are designed to engage and lock within through-holes 20 of the plate, to form plate/bushing assembly 101, 201. As detailed below, the bushing 50, 150 is first inserted into the plate 100, 200 in a direction about perpendicular to the plate 100, 200, i.e., with the axis of the bushing oriented about perpendicularly to the axis of through-hole 20 of the plate, so that the center of the bushing is aligned with the center of the through-hole, and a flat on a lateral side of the bushing is aligned with a corresponding flat on an inner wall of the through-hole. At this step, the bushing is in an unlocked position. The bushing is then rotated within the through-hole 20 of the plate so that the top surface of the bushing is about parallel to the top surface of the plate, preferably in the same plane, to lock and constrain the bushing within the through-hole of the plate. At this step, the bushing is in a locked position. Unlocking of the bushing from the plate requires a manual step of physically rotating the bushing within the through-hole, so that the axis of the bushing is again oriented about perpendicularly to the axis of through-hole 20 of the plate, to allow the bushing to be pulled from the through-hole.

Figure 1B:
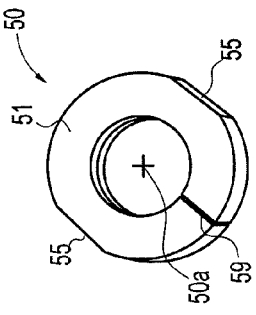
FIG. 1B illustrates a cross-sectional view of bone plate of FIG. 1A taken along line A-A.

As shown in FIG. 1A, bone plate 100 has a body 10 provided with at least one through-hole (screw hole) 20. Body 10 may be formed of a metal, preferably titanium. As shown in FIGS. 1A-B, bone plate 100 has through-hole (screw hole) 20 with a generally spherical cross-section provided with a flat 22 on the inner wall of the through-hole. Flat 22 may have a square or rectangular configuration (surface area) and is configured to be aligned with a corresponding flat 55 on the bushing, as described below.

Figure 2A:
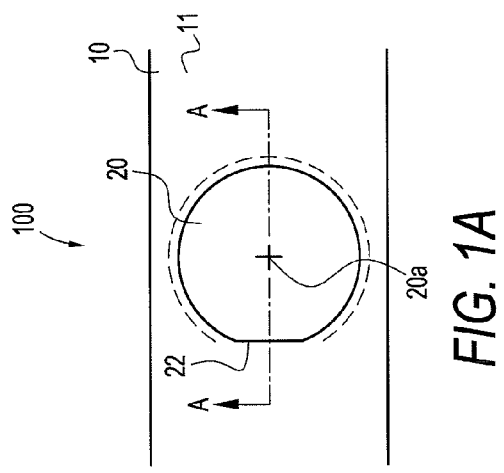
FIG. 2A illustrates a top view of a bushing of the present invention for use with the bone plate of FIG. 1A, and according to a first embodiment.
Figure 2B:
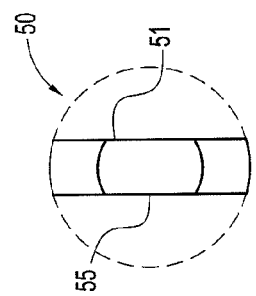
FIG. 2B illustrates a left-side lateral view of the bushing of FIG. 2A.
Figure 2C:
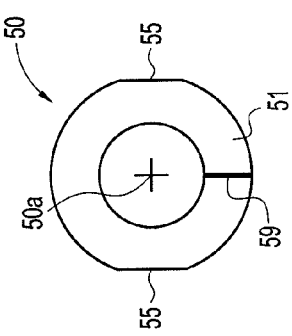
FIG. 2C illustrates a perspective view of the bushing of FIG. 2A.

FIGS. 2A-C illustrate various views of bushing 50 of the present invention that is configured to engage the through-hole (screw hole) 20 of the plate 100 of FIG. 1, and to further allow a screw to lock at variable angles relative to body 10 of the plate. Bushing 50 may have a general donut-shape configuration, with upper and lower surfaces preferably planar, and sized so that it is inserted into the through-hole 20 and locked therein, as detailed below. Bushing 50 is provided with a generally spherical outer shape having at least one flat 55 (preferably, with two flats 55 as shown in FIG. 2) and a small cut (split) 59. Flat 55 may have a square or rectangular configuration (surface area) and is configured to be aligned with flat 22 on the plate. Preferably, flat 22 has a geometry similar to that of flat 55, and surface area about equal to the surface area of the flat 55.

During assembly with the plate to form assembly 101, as illustrated in FIG. 3A, the bushing 50 is first inserted by introducing the bushing in a direction about perpendicular to the through-hole of the plate, so that a longitudinal axis of the bushing is about perpendicular to the longitudinal axis of the through hole; aligning the center of the bushing with the center of the through-hole; and aligning the flat 55 of the bushing with the flat 22 of the plate, to place the bushing in the proper orientation for assembly.

As shown in FIG. 3B, rotating the bushing about 90 degrees allows the bushing to be constrained within the through-hole of the plate. The alignment of the flat 55 of the bushing 50 and the flat 22 of the bone plate 10 prevents rotation of the bushing within the through-hole 20. The bushing 50 is constrained within bone plate 10 due to the diameter of the bushing being larger than the diameter of the through-hole as shown in FIG. 3D. In this orientation, a top surface 51 of the bushing 50 is about parallel to a top surface 11 of the plate 100, preferably in the same plane, to lock and constrain the bushing 50 within the through-hole 20 of the plate 100 (as shown in FIGS. 3B-3D).

Once positioned within the through hole 20, the bushing 50 cannot rotate, or dislodge from, or otherwise come out of, the plate 100 unless the bushing 50 is turned again about 90 degrees relative to the plate. The flat 55 on the bushing 50 mates with the flat 22 on the internal wall of the hole (screw hole) 20 to prevent it from rotating within the screw hole 20. This aspect is important to avoid the need for a bushing guide during insertion of the screw. As the screw is inserted through the bushing, the head of the screw expands the bushing against the plate, locking the bushing to the plate. As the screw is advanced, the outward taper of the screw head spreads the split (small cut) 59 of the bushing, causing the bushing to become locked due to the frictional interference between the outer surface of the bushing and an inner surface (the walls) of the through-hole 20 of the plate 100. The process is repeated for a plurality of bushings and screws, and for each bushing individually, until the plate is secured to the bone.

During the screw insertion, as a result of the alignment/locking design of the bushing and through-hole, the bushing is prevented from rotating and/or dislodging from the screw hole. The bushing design also allows the screw to be locked at variable angles. If desired, the bushing is provided with internal threads corresponding to external threads on the body of the screw, to facilitate advancement of the screw through the passageway of the bushing.

Referring now to FIGS. 5A-C, bushing 150 according to a second exemplary embodiment of the present invention may be provided with an optional post 180 to prevent the bushing 150 from rotating. In an exemplary embodiment, post 180 extends about perpendicular to flat 155. Referring now to FIGS. 4A-B, bone plate 210 of the present invention may have a modified through-hole 220 to accommodate the bushing 150 with post 180. As shown, bone plate 210 has a through-hole 220 having a generally spherical shape with a slot 280 sized to fit the post 180 of bushing 150. The slot 280 captures the post 180 of the bushing 150 and prevents rotation of the bushing during screw insertion.

FIGS. 6A-D illustrate exemplary steps of assembling the bushing 150 to the bone plate 210 to form assembly 201. During assembly with the plate, and as illustrated in FIG. 6A, the bushing 150 is first inserted by introducing the bushing in a direction about perpendicular to the through-hole 220 of the plate, so that a longitudinal axis of the bushing is about perpendicular to the longitudinal axis of the through hole; aligning the center of the bushing with the center of the through-hole; and aligning the post 180 of the bushing with the slot 280 of the plate, placing the bushing in the proper orientation for assembly. As shown in FIG. 6B, rotating the bushing about 90 degrees allows the bushing to be constrained within the through-hole of the plate. The alignment of the post 180 of the bushing 150 and the slot 280 of the bone plate 10 prevents rotation of the bushing within the through-hole 220. The bushing 150 is constrained within bone plate 210 due to the diameter of the bushing being larger than the diameter of the through-hole as shown in FIG. 6D.

The present invention also provides a method of providing a bushing/plate assembly by inter alia: (i) providing a bushing with an alignment/locking mechanism configured to mate with a corresponding alignment/locking mechanism of an inner wall of a through-hole of a bone plate, when the bushing is inserted into the plate; (ii) introducing the bushing in a direction about perpendicular to the through-hole of the plate, so that the bushing is about perpendicular to the through hole, and the center of the bushing is aligned with the center of the through-hole; and (iii) rotating the bushing about 90 degrees so that the bushing is captured within the through-hole of the plate, and the alignment/locking mechanism of the bushing is aligned with the alignment/locking mechanism of the plate. The alignment/locking mechanism of the bushing may be a flat, a pin, or a combination of a flat and a pin. The alignment/locking mechanism of the wall of the through-hole of the plate may be a flat, a pin slot, or a combination of a flat and a pin slot.

The present invention also provides a method of assembling a bushing to a bone plate by inter alia: (i) providing a bushing with a first flat on the outer wall of the bushing, and providing a second flat on an inner wall of a through-hole of a bone plate, the second flat being configured to align with the first flat when the bushing is inserted into the plate; (ii) introducing the bushing in a direction about perpendicular to the through-hole of the plate, so that a longitudinal axis of the bushing is about perpendicular to a longitudinal axis of the through hole, and the center of the bushing is aligned with the center of the through-hole; and (iii) rotating the bushing about 90 degrees so that the bushing is captured within the through-hole of the plate (with the first flat aligned with the second flat).

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A locking plate assembly for engagement with a bone, comprising:
    a plate comprising a body and at least one through-hole, the at least one through-hole having an inner wall with a flat; and
    a bushing comprising an exterior surface having a substantially spherical shape with at least one bushing flat and a passageway comprising an interior surface, the bushing flat engaging the flat of the through-hole to prevent rotation of the bushing relative to the through-hole.

2. The assembly of claim 1, wherein the plate has one flat and the bushing has two bushing flats.

3. The assembly of claim 2, wherein the two bushing flats are diametrically and symmetrically located relative to a center of the bushing.

4. The assembly of claim 1, wherein the flat of the through-hole of the plate has a surface area about equal to a surface area of the bushing flat.

5. The assembly of claim 1, wherein at least one of the flat of the through-hole and the bushing flat has one of a rectangular, square or trapezoidal configuration.

6. The assembly of claim 1, wherein the bushing is expandable and is provided with a slit extending completely through a wall of the bushing.

7. The assembly of claim 1, wherein the exterior surface of the bushing and the wall of the through-hole are substantially spherical in a complementary manner, except where the flats are located.

8. The assembly of claim 1, wherein the plate further comprises a pin slot extending from the flat of the through-hole and into the body.

9. The assembly of claim 8, wherein the pin slot of the plate engages a corresponding pin of the bushing, the pin of the bushing extending about perpendicular to the bushing flat.

10. A locking plate apparatus for engagement with a bone, comprising:
    a plate comprising a body and at least one through-hole, the at least one through-hole having an inner wall with a first alignment/locking mechanism; and
    an expandable bushing comprising an exterior surface having a substantial spherical shape with a second alignment/locking mechanism, a passageway comprising an interior surface, and a slot extending through a wall of the bushing, wherein, when the bushing is inserted into the through-hole, the first alignment/locking mechanism engages the second alignment/locking mechanism and prevents rotation of the bushing relative to the through-hole, wherein the bushing is secured within the through-hole by first inserting the bushing within the through-hole in a direction about perpendicular to the through-hole so that a central axis of the bushing is oriented about perpendicularly to a central axis of the through-hole, and then rotating the bushing by about 90 degrees, so that the first alignment/locking mechanism mates with the second alignment/locking mechanism.

11. The apparatus of claim 10, wherein the first alignment/locking mechanism comprises a first cutout on an inner wall of the through-hole and wherein the second alignment/locking mechanism comprises a second cutout on the exterior surface of the bushing, the surface area and geometry of the first cutout being about equal to the surface area and geometry of the second cutout.

12. The apparatus of claim 11, wherein the first alignment/locking mechanism further comprising a pin slot extending from the first cutout and into the body of the plate, and wherein the second alignment/locking mechanism further comprises a pin extending about perpendicularly to the second cutout and configured to be seated within the pin slot.

13. The apparatus of claim 10, wherein the bushing is removed from the through-hole by first rotating the bushing for about 90 degrees so that the bushing is about perpendicular to the through-hole, and the first alignment/locking mechanism is not in alignment with the second alignment/locking mechanism, and then pulling the bushing from the through-hole.

14. A method of engaging a locking plate to a bone, comprising the steps of:
    positioning a locking plate against the bone, the locking plate comprising a body and at least one through-hole, the at least one through-hole having an inner wall with a flat;
    inserting an expandable bushing in at least one through-hole of the plate so that the expandable bushing is oriented about perpendicularly to the plate in that a central axis of the bushing is oriented about perpendicularly to a central axis of the at least one through-hole of the plate, the expandable bushing comprising an exterior surface with at least one bushing flat and a passageway comprising an interior surface; and
    subsequently, rotating the expandable bushing for about 90 degrees, so that a top surface of the bushing is about parallel to a top surface of the plate and the bushing flat mates with the flat of the through-hole to prevent rotation of the bushing relative to the through-hole.

15. The method of claim 14, wherein, when the expandable bushing is rotated for about 90 degrees, a top surface of the bushing is about planar to a top surface of the plate.

16. The method of claim 14, further comprising the step of inserting an elongated anchoring member through the passageway of the expandable bushing and into the bone.

17. The method of claim 16, wherein the step of preventing rotation of the bushing relative to the through-hole is conducted without a bushing guide during insertion of the anchoring member.

18. The method of claim 14, wherein the plate is further provided with a pin slot extending away from the flat and into the body of the plate, and wherein the bushing further comprises a pin with dimensions about equal to the dimensions of the pin slot, to permit secure engagement of the pin within the pin slot.

19. The method of claim 14, wherein the step of inserting the expandable bushing in the at least one through-hole of the plate further comprises the steps of aligning a center of the through-hole with a center of the bushing, and aligning the flat of the through-hole with the bushing flat.

* * * * *